United States Patent [19]

Arnold

[11] Patent Number: 4,995,857
[45] Date of Patent: Feb. 26, 1991

[54] LEFT VENTRICULAR ASSIST DEVICE AND METHOD FOR TEMPORARY AND PERMANENT PROCEDURES

[76] Inventor: John R. Arnold, 666 Seminole Dr., Winter Park, Fla. 32789

[21] Appl. No.: 334,934

[22] Filed: Apr. 7, 1989

[51] Int. Cl.⁵ ............................................. A61F 1/24
[52] U.S. Cl. .......................................... 600/16; 623/3
[58] Field of Search ........................ 600/16, 17; 623/3

[56] References Cited

U.S. PATENT DOCUMENTS

| | | | |
|---|---|---|---|
| 4,625,712 | 12/1986 | Wampler | 623/3 |
| 4,662,355 | 5/1987 | Pieronne et al. | 600/17 |
| 4,704,121 | 11/1987 | Moise | 623/3 |
| 4,779,614 | 10/1988 | Moise | 600/16 |
| 4,846,152 | 5/1989 | Wampler et al. | 623/3 |

Primary Examiner—Francis Jaworski
Assistant Examiner—George Manuel
Attorney, Agent, or Firm—Duckworth, Allen, Dyer & Doppelt

[57] ABSTRACT

A left ventricular assist device and method is utilized to relieve the hemodynamic burden on a diseased left ventricle in the heart of a patient by inserting a shunt having an impellar for effectuating a substantially non-turbulent, non-traumatic flow of blood either from the left atrium or the patient's venous system, directly into the patient's arterial system. The impellar shunt may be utilized in either a temporary or permanent implant setting.

21 Claims, 2 Drawing Sheets

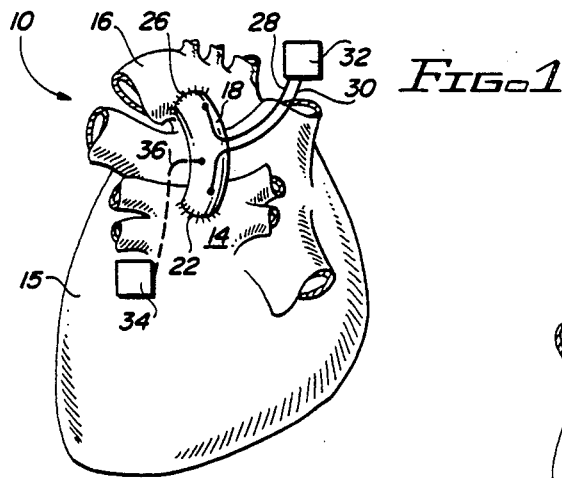
FIG. 1
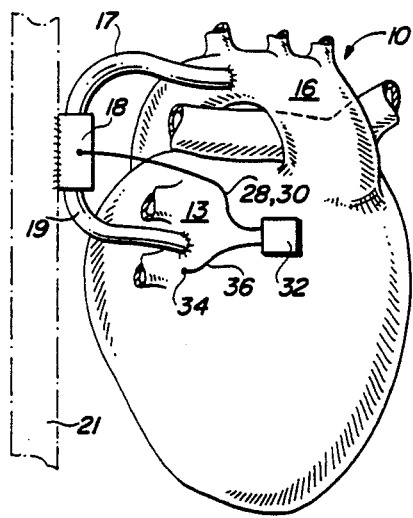
FIG. 2a
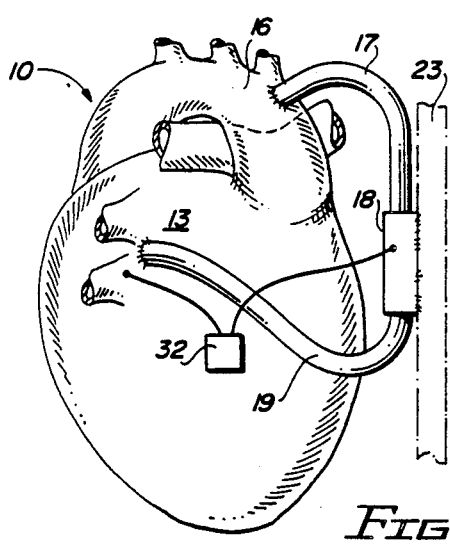
FIG. 2b
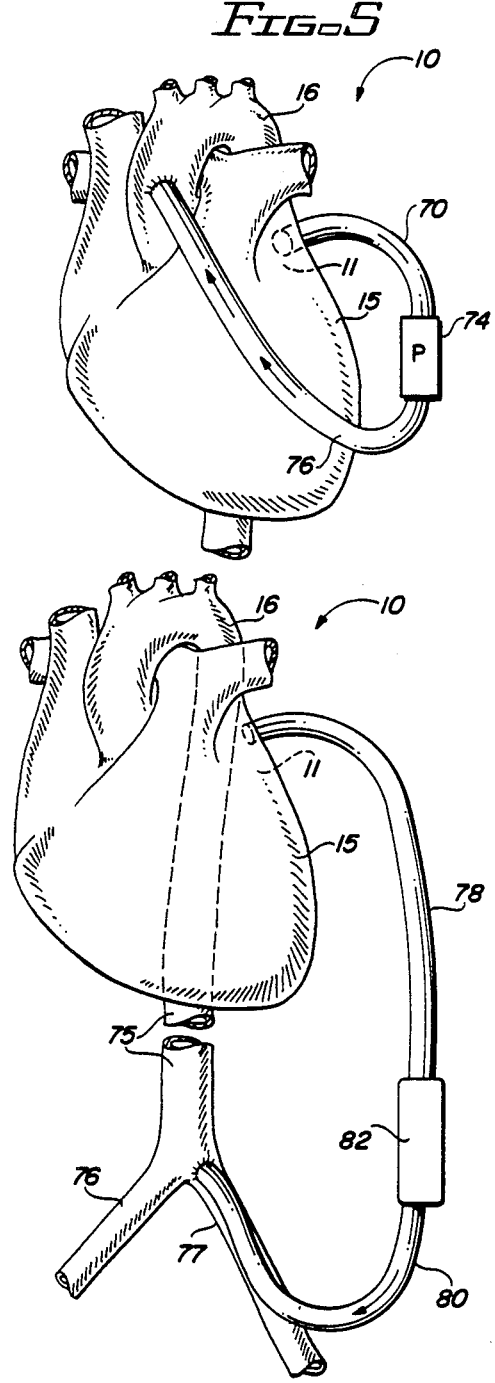
FIG. 5
FIG. 6

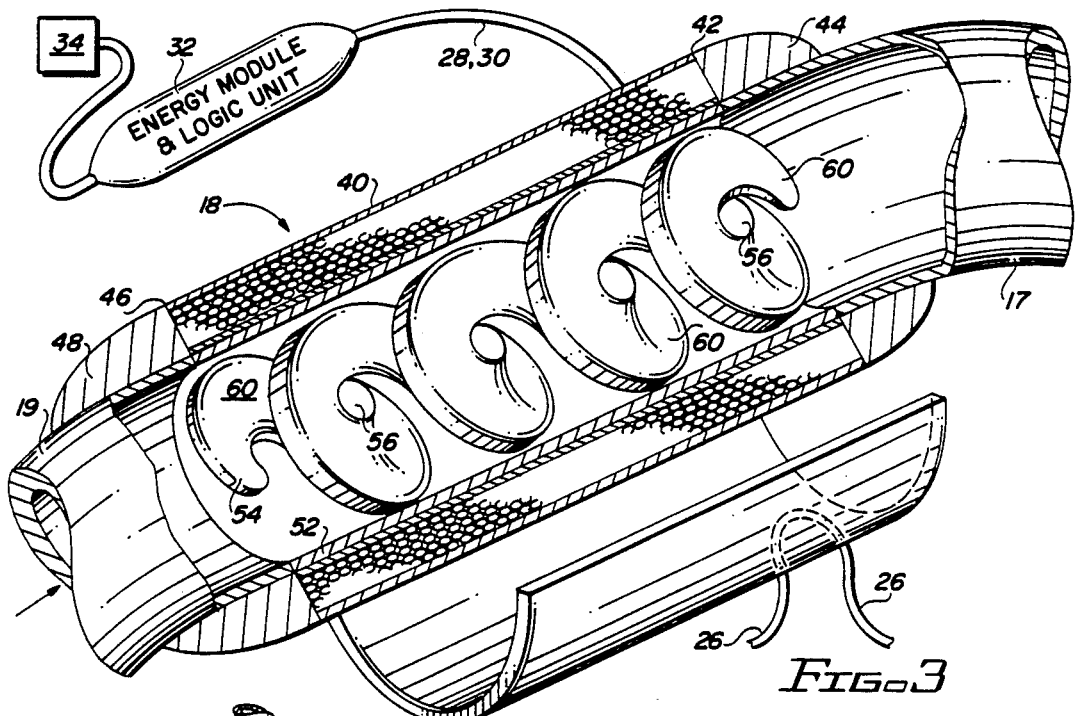
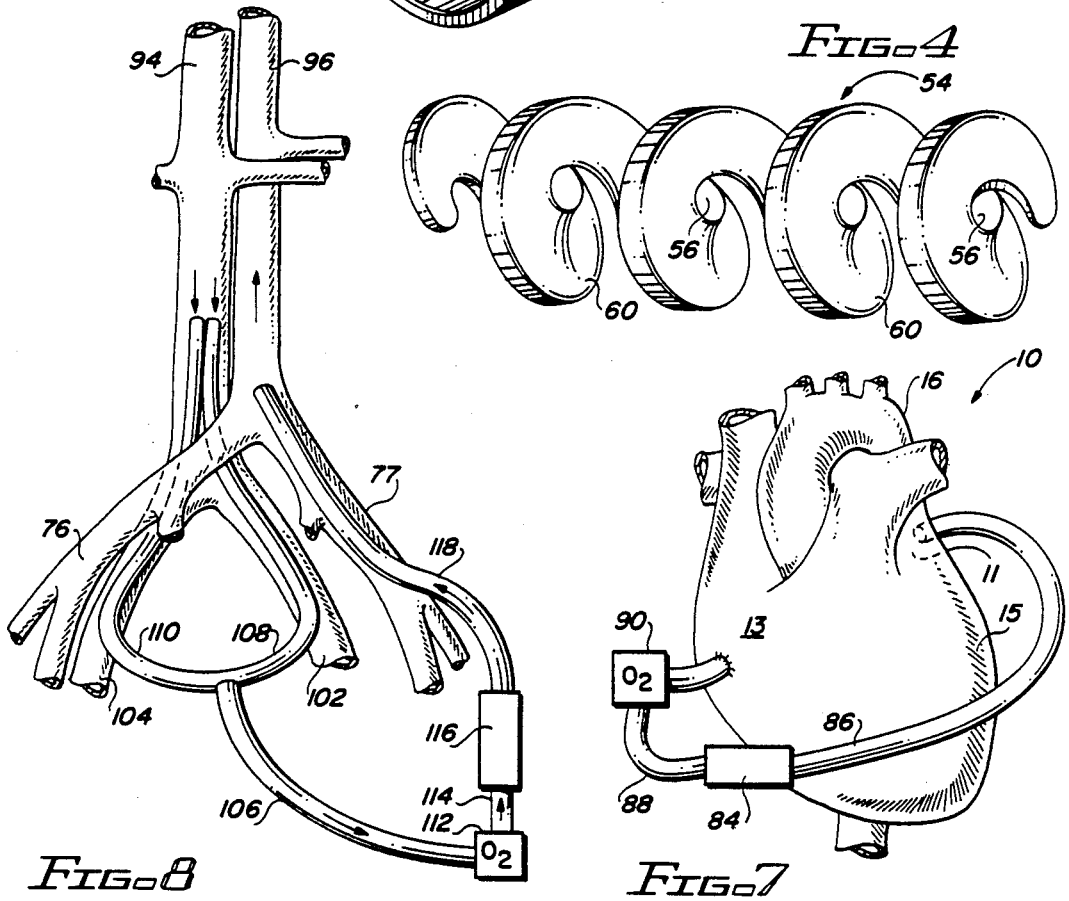

LEFT VENTRICULAR ASSIST DEVICE AND METHOD FOR TEMPORARY AND PERMANENT PROCEDURES

BACKGROUND OF THE INVENTION

The present invention relates generally to methods and apparatus for treating a diseased human heart, and in particular to a method and apparatus for treating a patient having a severely diseased left ventricle.

The human heart has four main chambers, the right and left ventricles and the right and left atria. From the right ventricle, blood is pumped through the pulmonary artery into the lungs, where the blood is oxygenated from the alveoli. The blood then returns from the lungs through the pulmonary veins into the left atrium. After passing through the mitral valve, the blood is then pumped out of the left ventricle and into the aorta and thence into the arteries of the body. The venous system then returns the blood to the right atrium via the inferior and superior vena cava. During diastole, the heart relaxes and blood fills the atria and ventricles. During systole, the right and left ventricles contract and drive the blood from the right ventricle into the lungs, and simultaneously from the left ventricle into the aorta and its branching arteries.

One type of heart ailment is commonly referred to in layman's terms as a "diseased left ventricle". This term is applied here to any heart disease in which the contractile properties of the left ventricle are impaired.

It is known that, even when a left ventricle of a patient is in a diseased condition, the left ventricle does not cease to function entirely; rather, the capacity of the left ventricle to deliver the proper amount of blood to the aorta is only partially reduced.

There have been recent suggestions for the insertion of pumping devices through the arterial system for relief of the diseased left ventricle, in order to provide mechanical assistance in delivering blood from the diseased left ventricle into the aorta.

In U.S. Pat. No. 4,105,016, Donovan discloses the use of a centrifugal blood pump in order to reduce the pressure in either the right or left ventricle in synchronism with the ventricular contractions of a diseased heart. The pump disclosed in the Donovan '016 patent is implanted in a parallel relationship with the ventricle to be assisted, and is run at a constant speed. When the ventricular pressure reaches a predetermined value, blood automatically begins to flow through the pump, thereby reducing the maximum allowable pressure in the ventricle being assisted.

In U.S. Pat. No. 4,688,998, Olsen et al disclose a ventricular assist pump utilizing a magnetically-suspended impeller inside a centrifugal flow tube. Other prior art centrifugal heart-assist pumps are also disclosed in the following United States patents: U.S. Pat. No. 3,647,324 to Rafferty et al.; Reissue No. 28,742 to Rafferty et al; and U.S. Pat. No. 3,608,088 to Dorman et al. Similar prior art is disclosed in an article by Tanaka et al, in an article entitled "A Compact Centrifugal Blood Pump for Extracorporeal Circulation: Design and Performance", *Transactions of the ASME*, Vol. 109, August 1987.

In the aforementioned patents to Rafferty et al, there is a detailed discussion of the complex makeup of blood and its constituents, and the deleterious effect on blood when it is subjected to shear action or other mechanical stresses; see Col. 2, lines 19-60 of U.S. Pat. No. 3,647,324.

SUMMARY OF THE INVENTION

The present invention is directed to a method, and associated apparatus, for relieving the hemodynamic burden on a diseased left ventricle in the heart of a patient. In a preferred embodiment, the method for achieving this goal includes the step of inserting a shunt which communicates directly between the interior of the patient's left atrium and the patient's arterial system, thus bypassing the left ventricle. A hollow-core impeller is positioned in the shunt, and actuated so as to effectuate a substantially non-turbulent, non-traumatic flow of blood from the left atrium into the arterial system. Such flow through the shunt may be in addition to the conventional flow which is ongoing from the patient's left ventricle into the aorta, so as to supplement that flow in order to reduce the stress on a diseased left ventricle.

When the shunt is used in a temporary setting (as, for example, during by-pass surgery), the shunt is preferably inserted between the left atrium and one of the patient's femoral arteries. In some temporary situations, the shunt may also be joined at the ascending aorta. When permanently implanted, the shunt is preferably inserted between the left atrium and the patient's ascending aorta.

In the preferred embodiment, the impeller is suspended centrally in the shunt and is rotated to effectuate the blood flow. The shunt preferably is of a generally cylindrical configuration with a longitudinal axis, and with the impeller comprising an auger having a longitudinal axis generally coaxial with the axis of the shunt and with the hollow core of the impeller extending axially along the auger. Suitably, the impeller is disposed in a casing having permanent magnets positioned about its periphery, and with the rotation of the auger casing being effectuated by a field coil surrounding the outside periphery of the casing and within the shunt.

In accordance with another aspect of the method of the present invention, the pressure in the patient's left atrium is monitored, and the flow of blood through the shunt is controlled dependent upon the pressure in the patient's left atrium. For example, when the pressure in the patient's left atrium exceeds a level of about twelve millimeters of mercury, then the flow of blood through the shunt may be increased, in order to relieve the stress on the left ventricle.

The apparatus of the present invention which achieves the method discussed above includes a generally tubular shunt dimensioned to fit between the wall of the patient's left atrium and the patient's ascending aorta. A sleeve of Dacron or Gortex is provided about each end of the shunt for permitting one end to be joined to the wall of the patient's left atrium and the other end to the patient's aorta, with the impeller being positioned in the shunt. Means are provided about the periphery of the shunt for rotating the impeller to effectuate the desired flow of blood between the patient's left atrium and the patient's aorta.

DESCRIPTION OF THE DRAWING

FIG. 1 is a perspective view illustrating the heart muscle, and the location of a permanently implanted shunt in accordance with the present invention.

FIGS. 2(a) and (b) are perspective views illustrating the heart and the location of the shunt of the present invention anchored to the skeletal frame.

FIG. 3 is an exploded perspective view, partially cut away, of the shunt in accordance with the present invention.

FIG. 4 is a side view of the impeller shown in FIG. 3.

FIG. 5 is a perspective illustrating the shunt of the present invention in temporary use during an open-chest surgical procedure.

FIG. 6, 7 and 8 are perspective views illustrating alternative uses for the shunt of the present invention during temporary surgical procedures.

DESCRIPTION OF THE PREFERRED EMBODIMENT

Referring now to FIG. 1, the heart is identified generally by reference numeral 10 and includes the left atrial chamber 14, and the aorta 16 which communicates with the left ventricle 15. In accordance with the present invention, a tubular shunt 18 is implanted between the interior of the left atrium 14 and the interior of the aorta 16. To achieve this, one end 20 of the shunt 18 is sewn with thread to the wall of the left atrium, and an appropriate incision made in the wall of the left atrium. Likewise, the second end 24 of the tubular shunt 18 is sewn with thread 26 to the aorta 16, and an appropriate incision made in the aorta to achieve blood flow between the left atrium 14 and the aorta 16 in accordance with this invention.

As will be described in greater detail below with reference to FIGS. 3 and 4, the shunt 18 is provided with an impeller for effectuating blood flow from the left atrium 14 into the aorta 16 in a non-turbulent, non-traumatic manner, through the use of an electric field coil surrounding the periphery of the shunt 18. To provide control and power to the electric field coil, a logic and power unit 32 is implanted in the patient's body at a location distal from the heart 10, and electric current is fed into the electric field coil via circuit lines 28, 30.

In accordance with another aspect of the method and apparatus disclosed herein, a conventional pressure transducer 34 is implanted in the left atrium 14, and communicates with the shunt 18 via circuit line 36.

The shunt 18 may also be anchored to a portion of the patient's skeletal frame; in FIG. 2(a), the shunt 18 is shown anchored to the spinal column 21. It is also suitable to anchor the shunt to the sternum 23, as shown in FIG. 2(b). In either instance, the feed lines 17 and 19 are utilized to conduct the blood between the shunt and the left atrium or the aorta, in the same manner as is shown in FIG. 1 above.

The details of the shunt and its associated impeller will now be described with reference to FIGS. 3 and 4.

The outside of the shunt may be covered with a conventional non-toxic implantable fabric 41. As shown in FIG. 3, the shunt 18 includes an internal cylindrical member 40 having flexible plastic sleeves 44 and 48 at the extremities thereof, to facilitate joinder at the respective locations of the left atrium 14 and aorta 16 via threads 22 and 26, at the respective ends 46 and 42 of the cylinder 40. An electric field coil 50 surrounds the tubular member 40, which is coupled to the lines 28, 30 in a conventional manner.

A second tubular member 52 is positioned within the first member 40, and is supported by low friction bearings (not shown) at the respective ends thereof. The tubular member 52 comprises an annular permanent magnet armature within the member 40. The impeller comprises an auger 54 anchored to the inside periphery of the member 52, and which has a central hole 56 extending longitudinally therethrough along the axis of the auger and the two coaxial tubular members 40 and 52. The auger 54 is preferably formed of a molded thermoplastic material, which is defined by a helical convolution 60, and a flat inside face 58. The convolution 60 is itself concave, as is shown at concavity 62 along each convolution. (Note FIG. 4). The internal cylindrical armature 52 is surrounded by a film of a fine lubricant, which is insulated by the end bearings.

As discussed above, the system of the present invention may also be utilized as a temporary left ventricle assist device. For example, immediately following open-heart surgery, the system as described above may be cannulated between the left atrial appendage and the ascending aorta as is shown in FIG. 5. There, the impeller pump housing 74 is connected via circulating tubing 70 and 72 between the left atrium 11 (shown with tubing 70 connected at the extremity of the left atrial appendage in FIG. 5) and the ascending aorta 16.

In situations where the patient has undergone open heart surgery, the system can be mounted externally to support the systemic circulation. Such an arrangement is shown in FIG. 6 where the impeller pump 82 is connected by a tubing 78, 80 between the left atrial appendage 11 and one of the femoral arteries 76, 77 which are in turn coupled with the descending aorta 75. In such an arrangement, it will be understood that the femoral artery 77 is simply cannulated percutaneously.

FIG. 7 illustrates a manner for using the shunt of the present invention in an open chest procedure. As shown in FIG. 7, the shunt 84 communicates between the left atrium 11 and the atrium 13 via tubing 86, 88 and 92 with a conventional oxygenation system 90 between the shunt 84 and the right atrium. In this configuration, blood flows out of the right atrium 13, through the oxygenator 90, the shunt 84 and into the left atrium 11 and is useful on a temporary basis during open chest procedures.

FIG. 8 illustrates a temporary use for the shunt of the present invention where it is more feasible not to cannulate the heart, as, for example, when the patient is in cardiogenic shock or acute cardio-pulmonary collapse. As shown, the shunt 116 communicates via tubing 106, 114 and 118 through oxygenator 112 between the femoral veins 102, 104 and the femoral arteries 76, 77. It will be understood that blood flow extends from the inferior vena cava 94, downwardly into the femoral veins 102, 104, through the branches 110, 108 of the tubing 106, through the oxygenator 112, the shunt 116, into the femoral arteries 76, 77 and thence into the aorta 96. In this configuration, the shunt 116 may also be utilized indirectly to relieve a diseased left ventricle temporarily during surgical procedures.

The function of the shunt 18 of the present invention will now be described.

The shunt 18 is initially inserted as shown in either FIG. 1, 2(a), 2(b), 5, 6, 7 or 8 so as to permit the flow of oxygenated blood into the patient's arterial system. It will of course be understood that the shunt 18 is only used when the patient has been determined to have a severely diseased left ventricle, requiring relief from the hemodynamic burden normally incurred by a healthy left ventricle.

After the auger 54 is actuated, the flow of blood from into the arterial system is facilitated in a substantially non-turbulent, non-traumatic manner, because all blood-contact surfaces of the auger 54 are in motion, pushing the blood in a central laminar flow. Additionally, the central passageway 56 relieves any pressure during movement of the auger 54, thereby avoiding the type of mechanical trauma to the blood which is discussed in the aforementioned prior art. The flat face 58 of the auger 54 further reduces the mechanical stress on the blood during the impelling of blood by the auger 54.

It will further be understood that the sensor 34 (FIG. 1), when used, monitors the pressure in the patient's left atrium, and controls the rate of flow of blood between the left atrium and the aorta, dependent upon the pressure. Any elevation of the left atrial pressure, as detected by the transducer 34, will induce a corresponding increase in the rate of rotation of the auger 54.

The manner in which the multiconvolutional auger 54 is mounted within the inner cylinder 52 eliminates a central shaft. All surfaces which are in contact with blood are therefore in motion at the same rate. This, combined with the central laminar flow generated by the shape of the impeller and the nonthrombogenic material used to create the impeller and its cylinder, protects blood by reducing friction and turbulence and avoiding stasis.

It will thus be understood that the shunt of the present invention may be utilized either as a permanent implant or in a temporary setting during the course of open heart or other surgical procedures, as well as emergency percutaneous insertion with cardio-pulmonary arrest or cardiogenic shock.

What is claimed is:

1. A method for relieving the hemodynamic burden on a diseased left ventricle in the heart of a patient, comprising the steps of:
    implanting a shunt within the patient's chest cavity between the interior of the patient's left atrium and the patient's major arterial system;
    positioning an impeller in said shunt;
    implanting a power source within the patient's chest cavity; and
    actuating said impeller with the power source so as to effectuate a substantially non-turbulent, non-traumatic flow of blood from the left atrium directly into the patient's arterial system.

2. The method recited in claim 1 further comprising the steps of:
    suspending said impeller centrally in said shunt; and
    rotating said suspended impeller to effectuate said blood flow.

3. The method recited in claim 2 wherein said shunt is generally cylindrical with a longitudinal axis therethrough.

4. The method recited in claim 3 wherein said impeller comprises an auger having a longitudinal axis generally coaxial with said shunt axis, and wherein said rotating step comprises rotating said auger about its longitudinal axis.

5. The method recited in claim 4 further comprising the step of mounting said auger within a cylindrical casing.

6. The method recited in claim 5 further comprising the steps of:
    affixing magnets to said casing; and
    placing an electrical field coil along said shunt perimeter for facilitating said suspension and rotation steps.

7. The method recited in claim 4 further comprising the step of extending an axial passageway centrally through said auger.

8. The method recited in claim 1, wherein said shunt is permanently implanted between the patient's left atrium and the patient's ascending aorta.

9. The method recited in claim 1, wherein said shunt is temporarily implanted between the patient's aorta and the patient's descending arterial system.

10. The method recited in claim 9, wherein the shunt is temporarily implanted between the patient's left atrium and one of the patient's femoral arteries.

11. A method for relieving the hemodynamic burden on a diseased left ventricle in the heart of a patient, comprising the steps of:
    implanting a shunt between the interior of the patient's left atrium and the patient's major arterial system;
    positioning an impeller in said shunt;
    actuating said impeller so as to effectuate a substantially non-turbulent; non-traumatic flow of blood from the left atrium directly into the patient's arterial system; and
    varying the actuation rate of said impeller responsive to pressure in said left atrium.

12. The method recited in claim 1 further comprising the step of anchoring said shunt to a portion of the patient's skeletal frame.

13. A method for relieving the hemodynamic burden on a diseased left ventricle in the heart of a patient comprising the steps of:
    implanting a portable shunt within the patient's chest cavity between the patient's femoral vein and the patient's femoral artery;
    implanting a power source with the shunt;
    effectuating a substantially non-turbulent, non-traumatic flow of blood through said shunt; and
    oxygenating the blood passing through said shunt.

14. The method recited in claim 13 wherein said shunt is generally tubular.

15. The method recited in claim 14 wherein said blood effectuating step comprises the steps of:
    placing an impeller in said shunt; and
    rotting said impeller.

16. The method recited in claim 15 further comprising the step of extending an axial passageway centrally through said auger.

17. Apparatus for relieving the hemodynamic burden on a diseased left ventricle in the heart of a patient, comprising:
    a generally tubular shunt dimensioned to extend between the wall of the patient's left atrium and the patient's arterial system;
    means for permitting said shunt to be joined at one end to the patient's left atrium and the other end to the patient's arterial system;
    an impeller in said shunt;
    an implantable electrical power source for operating the impeller; and
    means responsive to the electrical power source about the periphery of said shunt for rotating said impeller to effectuate a flow of blood between the patient's left atrium and the patient's arterial system through said shunt when inserted.

18. The apparatus recited in claim 17 wherein said impeller includes a central passageway therethrough.

19. Apparatus for relieving the hemodynamic burden on a diseased left ventricle in the heart of a patient, comprising:

a generally tubular shunt dimensioned to extend between the wall of then patient's left atrium and the patient's arterial system;

means for permitting said shunt to be joined at one end to the patient's left atrium and the other end to the patient's arterial system;

an impeller in said shunt;

means about the periphery of said shunt for rotating said impeller to effectuate a flow of blood between the patient's left atrium and the patient's arterial system through said shunt when inserted;

pressure monitoring means for detecting the pressure in the patient's left atrium; and means for controlling the rotation of said impeller responsive to said pressure detection means.

20. The apparatus recited in claim 17 wherein said impeller comprises an auger having a central passageway extending longitudinally through said tubular shunt.

21. The apparatus recited in claim 20 wherein said auger is further defined by a helical convolution having a concave surface and a generally flat face defining said central passageway.

* * * * *